(12) United States Patent
Yoon et al.

(10) Patent No.: US 8,207,282 B2
(45) Date of Patent: Jun. 26, 2012

(54) BIFUNCTIONAL ORGANOLITHIUM INITIATOR AND CONJUGATED DIENE COPOLYMERS PREPARED USING THE SAME

(75) Inventors: Du Weon Yoon, Seosan-si (KR); Tae Chul Lee, Daejeon (KR); Jeong Hyun Noh, Seoul (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 13/120,361

(22) PCT Filed: Sep. 18, 2009

(86) PCT No.: PCT/KR2009/005343
§ 371 (c)(1),
(2), (4) Date: Jun. 6, 2011

(87) PCT Pub. No.: WO2010/035990
PCT Pub. Date: Apr. 1, 2010

(65) Prior Publication Data
US 2012/0101212 A1    Apr. 26, 2012

(30) Foreign Application Priority Data
Sep. 23, 2008   (KR) .................. 10-2008-0093381

(51) Int. Cl.
*C07F 1/02* (2006.01)
(52) U.S. Cl. .................. 526/173; 526/180; 546/255
(58) Field of Classification Search .................. 526/173, 526/180; 546/255; *C07F 1/02*
See application file for complete search history.

(56) References Cited

U.S. PATENT DOCUMENTS

| | | | | |
|---|---|---|---|---|
| 3,278,617 A | * | 10/1966 | Kahle et al. | 260/665 R |
| 3,644,314 A | * | 2/1972 | Akira | 526/180 |
| 3,725,368 A | * | 4/1973 | Morrison et al. | 526/180 |
| 3,954,894 A | | 5/1976 | Kamienski et al. | |
| 4,067,917 A | | 1/1978 | Sigwalt et al. | |
| 4,161,494 A | | 7/1979 | Sigwalt et al. | |
| 4,172,190 A | | 10/1979 | Tung et al. | |
| 4,182,818 A | | 1/1980 | Tung et al. | |
| 4,196,153 A | | 4/1980 | Tung et al. | |
| 4,680,407 A | | 7/1987 | Roggero | |
| 5,149,457 A | * | 9/1992 | Smith | 252/182.12 |
| 5,171,800 A | * | 12/1992 | Bronstert | 526/173 |
| 5,523,371 A | | 6/1996 | Lawson et al. | |

FOREIGN PATENT DOCUMENTS

| | | | |
|---|---|---|---|
| EP | 0476640 | | 3/1992 |
| EP | 0626278 | | 11/1994 |
| GB | 2092163 A | * | 8/1982 |
| JP | 06-279515 A | | 10/1994 |
| JP | 2004-182894 A | | 7/2004 |
| KR | 10-1996-0041213 A | | 12/1996 |
| KR | 10-0788111 B1 | | 12/2007 |

OTHER PUBLICATIONS

Kauffmann Selective Metalation of 1,2-Bis(6-methyl-2-pyridyl)-ethane and its Preparative Uses. Angew. Chem. Internat. Edit., 1970, vol. 9, No. 10, pp. 808-809).*

* cited by examiner

*Primary Examiner* — Milton I Cano
*Assistant Examiner* — Brieann R Fink
(74) *Attorney, Agent, or Firm* — McKenna Long & Aldridge LLP

(57) ABSTRACT

A novel polymeric compound is provided. The polymeric compound is highly compatible with reinforcing materials. Particularly, the polymeric compound is highly miscible with inorganic reinforcing materials in the manufacture of a tire. Further provided is a novel bifunctional initiator necessary to prepare the polymeric compound. The bifunctional initiator contains amine moieties. Active ends of the polymer are modified with an alkoxysilane compound. The polymer has an improved affinity for carbon black and silica as reinforcing materials in the manufacture of a tire. Therefore, the use of the polymer can achieve desired physical properties required in a tire, e.g., high wet traction, low rolling resistance and high tread wear.

9 Claims, 2 Drawing Sheets

BIFUNCTIONAL ORGANOLITHIUM INITIATOR AND CONJUGATED DIENE COPOLYMERS PREPARED USING THE SAME

This application claims the priority to PCT/KR2009/005343 filed on Sep. 18, 2009 and Korean Patent Application No. 10-2008-0093381 filed on Sep. 23, 2008, all of which are hereby incorporated by reference in their entirety.

BACKGROUND OF THE INVENTION

1. Field of the Invention

The present invention relates to a polymerization initiator having a novel structure and conjugated diene polymers prepared using the polymerization initiator.

2. Description of the Related Art

Generally, the single use of a rubber as a tire material is insufficient to achieve desired physical properties of the tire. For the purpose of enhancing the physical properties (e.g., tread wear and frictional force) of a tire, it is common practice to add various reinforcing materials in the manufacture of the tire. A mixture of carbon black as an organic reinforcing material and silica as an inorganic reinforcing material is currently used in the manufacture of tires.

Nevertheless, several problems have been encountered in the use of the reinforcing materials. One of the problems is poor compatibility between the reinforcing materials and tire rubbers. This poor compatibility may make the reinforcing materials immiscible with the rubbers, leading to deterioration in the physical properties of the finished tire. On the contrary, good compatibility between reinforcing materials and rubbers in the manufacture of tires can ensure improved tread wear, reduced rolling resistance and improved wet traction of the tires.

Under such circumstances, various methods have been proposed to improve the compatibility of reinforcing materials, particularly, carbon black and silica with conjugated diene polymers. Of these, a representative method is to substitute the ends of a polymer with functional groups that have a high affinity for reinforcing materials. For example, one end of a polymer is modified with an amine compound to improve the compatibility with carbon black as an organic reinforcing material and the other end thereof is modified with a compound having another functional group to improve the compatibility with silica as an inorganic reinforcing material.

Methods for introducing functional groups into polymers can be largely divided into two methods: the first method is to modify one end of a polymer with different compounds and the second method is to use an initiator having one or more functional groups to introduce the functional groups into a polymer.

According to the second method, active ends of the polymer other than the initiator moiety can be modified with another functional compound, and as a result, both ends of the polymer can be modified. In comparison with the substitution of one end of the polymer, the modification of both ends of the polymer is advantageous in that the compatibility between the polymer and one or more reinforcing materials can be maximized.

Prior art techniques for modifying both ends of a polymer with a monofunctional initiator containing at least one amine moiety can be found in the literature, for example, see EP 0,476,640, EP 0,626,278 and U.S. Pat. No. 5,523,371.

Prior art techniques for modifying both ends of a polymer with a bifunctional initiator can be found in the literature, for example, see U.S. Pat. Nos. 4,182,818 and 4,196,153.

Prior art techniques regarding organolithium polymerization initiators can be found in the literature, for example, see U.S. Pat. Nos. 4,067,917, 4,161,494, 4,172,190 and 3,954,894.

There are large differences between the prior art techniques disclosed in the references and the present invention relating to novel organolithium compounds and compounds including the organolithium compounds.

As described above, there is a need to develop novel polymers that are highly miscible with inorganic reinforcing materials in the manufacture of tires. Thus, the inventors of the present invention have endeavored to develop a rubber that is compatible with carbon black as well as silica, and as a result, have found that a rubber produced by modifying the ends of a novel bifunctional initiator containing amine moieties with a silane compound showed greatly improved tread wear and dynamic physical properties, compared to other rubber products using only silica as a reinforcing material. The present invention has been accomplished based on this finding.

SUMMARY OF THE INVENTION

The present applicant intends to provide a novel polymeric compound that is highly miscible with carbon black and silica as reinforcing materials in the manufacture of a tire, a method for preparing the polymeric compound, a novel polymerization initiator necessary to prepare the polymeric compound, and a method for preparing the polymerization initiator.

According to an aspect of the present invention, there is provided an organolithium compound represented by Formula 1:

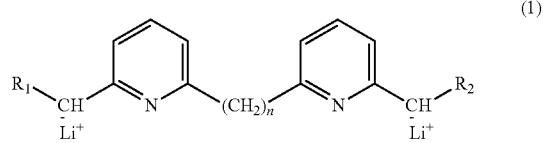

wherein $R_1$ and $R_2$, which may be the same or different, each independently represent a $C_1$-$C_6$ alkyl group, and n is an integer in the range of 1 to 14.

In an embodiment, the organolithium compound of Formula 1 is used as a polymerization initiator.

According to another aspect of the present invention, there is provided an organolithium compound represented by Formula 2:

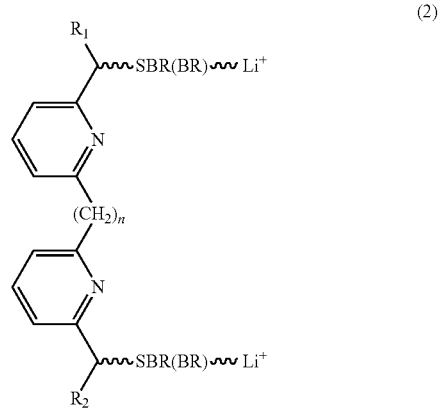

wherein $R_1$ and $R_2$, which may be the same or different, each independently represent a $C_1$-$C_6$ alkyl group, and n is an integer in the range of 1 to 14.

According to another aspect of the present invention, there is provided a compound represented by Formula 3:

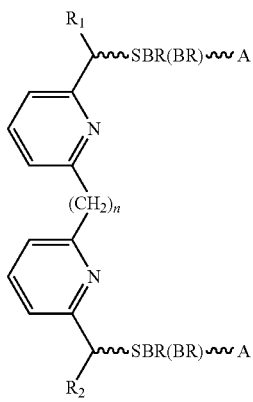

(3)

wherein $R_1$ and $R_2$, which may be the same or different, each independently represent a $C_1$-$C_6$ alkyl group, n is an integer in the range of 1 to 14, and each A is an alkoxysilane group.

In an embodiment, the compound is used as a tire material.

According to another aspect of the present invention, there is provided a composition comprising the compound of Formula 3 and one or more reinforcing materials.

In an embodiment, the composition further comprises one or more additives.

In an embodiment, the composition is used as a tire material.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Figure 1:
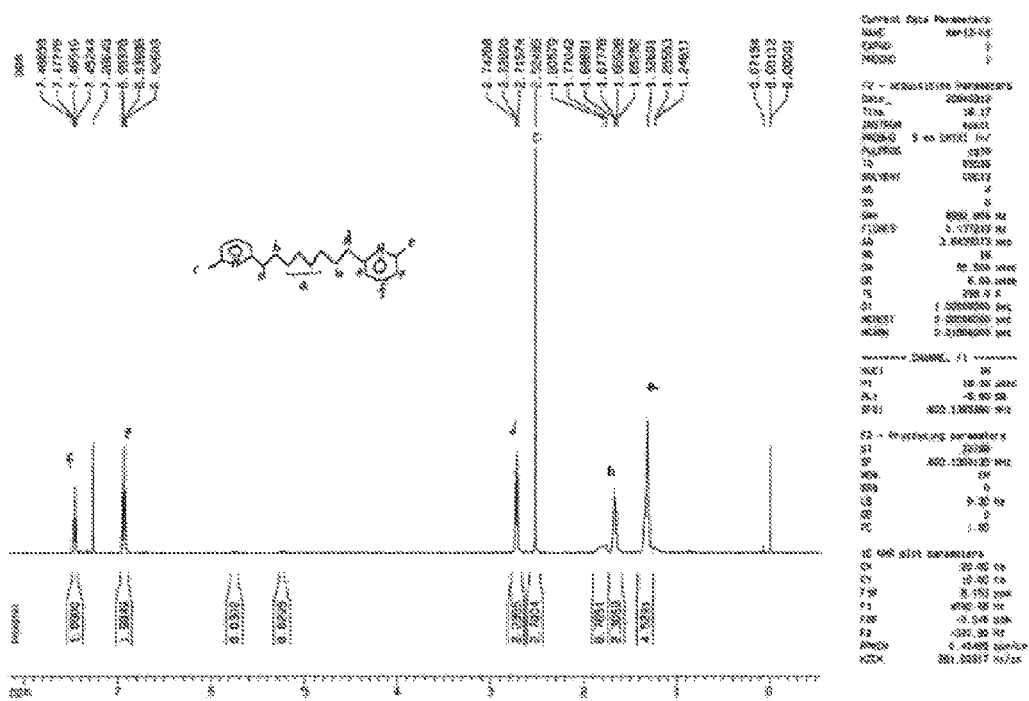
FIG. 1 is a $^1$H NMR spectrum of a compound prepared in Synthesis Example 1-(1)

Exemplary embodiments of the present invention will now be described in detail.

The present invention provides an organolithium compound represented by Formula 1:

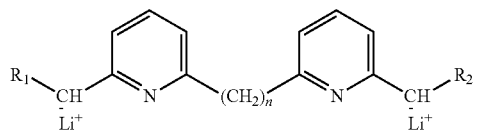

(1)

wherein $R_1$ and $R_2$, which may be the same or different, each independently represent a $C_1$-$C_6$ alkyl group, and n is an integer in the range of 1 to 14.

The organolithium compound of Formula 1 is a novel compound and is also a novel polymerization initiator. Particularly, the organolithium compound of Formula 1 can be used as a polymerization initiator for the preparation of a polymer that is highly miscible with one or more reinforcing materials in the manufacture of a tire. The organolithium compound of Formula 1 is in the form of a salt in which the lithium cations are bonded to the carbon anions.

Any known polymerization process may be used to prepare a polymer using the organolithium compound of Formula 1. There is no particular limitation on the preparation process. Solution polymerization is preferred because the temperature of a polymerization system is easily controlled and monomers are easily recovered.

It is estimated that anionic polymerization occurs when the organolithium compound of Formula 1 according to the present invention is used as an initiator. Specifically, after the lithium cations are separated from the organolithium compound of Formula 1 in the form of a salt, anionic polymerization occurs continuously at the carbon anions.

The present invention also provides an organolithium compound represented by Formula 2:

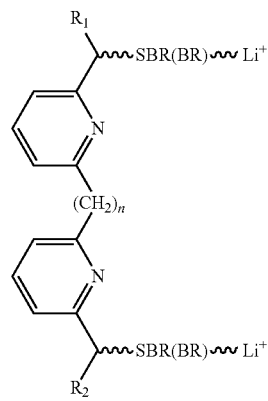

(2)

wherein $R_1$ and $R_2$, which may be the same or different, each independently represent a $C_1$-$C_6$ alkyl group, and n is an integer in the range of 1 to 14.

The compound of Formula 2 can be prepared by polymerization of 1,3-butadiene alone or styrene and 1,3-butadiene using the organolithium compound of Formula 1 as a polymerization initiator. In Formula 2, SBR and BR are abbreviations for styrene-butadiene rubber and butadiene rubber, respectively, which are obvious to those with ordinary knowledge in the art to which the invention belongs.

The present invention also provides a compound represented by Formula 3:

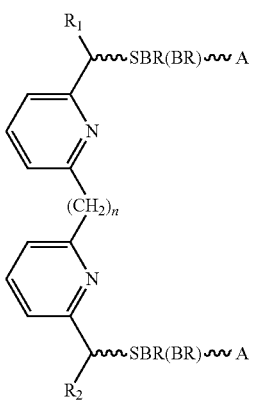

(3)

wherein $R_1$ and $R_2$, which may be the same or different, each independently represent a $C_1$-$C_6$ alkyl group, n is an integer in the range of 1 to 14, and each A is an alkoxysilane group.

The compound of Formula 3 can be prepared by reacting the compound of Formula 2 with a compound having at least one alkoxysilane group. All kinds of alkoxysilane compounds known to those with ordinary knowledge in the art to which the belongs may be used in the present invention. (3-Glycidoxypropyl)trimethoxysilane is more preferred due to its high affinity for silica (see Examples Section).

The present invention also provides a composition suitable for use as a tire material which comprises the compound of Formula 3 and at least one reinforcing material. Optionally, the composition may further comprise another reinforcing material and at least one additive.

The reinforcing material serves to improve the physical properties (e.g., tread wear) of a finished tire. As the reinforcing material, there may be exemplified silica or carbon black.

The compound of Formula 3 is terminated with alkoxysilane groups to achieve high miscibility with silica. Particularly, when the compound of Formula 3 is used as a tire material, its high miscibility with silica as a reinforcing material ensures desired physical properties (e.g., improved wet traction, reduced rolling resistance and improved tread wear) of a finished tire.

The additive is a compound that improves the physical properties of a tire or makes the miscibility of the compound of Formula 3 with various other compounds better. All kinds of additives widely known to those with ordinary knowledge in the art to which the invention belongs may be used in the present invention, and non-limiting examples thereof include sulfur, vulcanization accelerators, plasticizers and antioxidants. Specific examples of such additives include sulfur, stearic acid, zinc oxide, N-tert-butyl-2-benzothiazole sulfenamide, process oil and paraffin wax.

EXAMPLES

Hereinafter, the present invention will be explained in detail with reference to the following examples. However, these examples serve to illustrate the present invention and are not intended to limit the scope of the invention.

In the following synthesis example, the organolithium compound of Formula 1 was prepared.

Synthesis Example 1

Preparation of Initiator of Formula 1

1-(1) Preparation of bis-1,8-{6-methyl-2-pyridyl}octane 2,6-Lutidine (4.3 g, 40.2 mmol) was dissolved in 40 ml of anhydrous tetrahydrofuran and triethylamine (4.06 g, 40.2 mmol) in a 250 ml three-neck round-bottom flask. The solution was cooled to −20° C. in a cooling bath, and then 14.5% n-butyl lithium (30 ml, 46 mmol) was added dropwise thereto. The solution turned deep red. After 1,6-dibromohexane (5.1 g, 20.1 mmol) was slowly added to the deep red solution, the cooling bath was removed. The resulting mixture was allowed to warm to room temperature, followed by stirring at room temperature for 1 hr. The reaction mixture was concentrated. The concentrate was dissolved in ethyl acetate, washed with water and brine, dried over anhydrous magnesium sulfate, and concentrated, affording crude bis-1,8-{6-methyl-2-pyridyl}octane.

The structure of the crude product was confirmed by $^1$H NMR analysis (FIG. 1). The spectral data for the crud product are as follows.

$^1$H NMR (CDCl$_3$): δ 1.32 (8H), 1.66 (4H), 2.52 (6H), 2.73 (4H), 6.94 (4H), 7.47 (2H)

1-(2) Preparation of bis-1,8-{6-ethyl-2-pyridyl}octane

The crude bis-1,8-{6-methyl-2-pyridyl}octane (4.8 g) was dissolved in 40 ml of anhydrous tetrahydrofuran and triethylamine (4.06 g, 40.2 mmol) in a 250 ml flask. The solution was cooled to −20° C. in a cooling bath, and then 14.5% n-butyl lithium (30 ml, 46 mmol) was added dropwise thereto. The solution turned deep red. After the deep red solution was cooled to 0° C., methyl iodide (6.0 g, 42 mmol) was added dropwise thereto. The cooling bath was removed. The resulting mixture was allowed to warm to room temperature, followed by stirring at room temperature for 1 hr. The reaction mixture was concentrated. The concentrate was dissolved in ethyl acetate, washed with water and brine, dried over anhydrous magnesium sulfate, and concentrated. The concentrate was purified by short column chromatography (stationary phase: silica gel, mobile phase: n-hexane/ethyl acetate (5/1)), yielding 5.3 g of bis-1,8-{6-ethyl-2-pyridyl}octane as a liquid.

Figure 2:
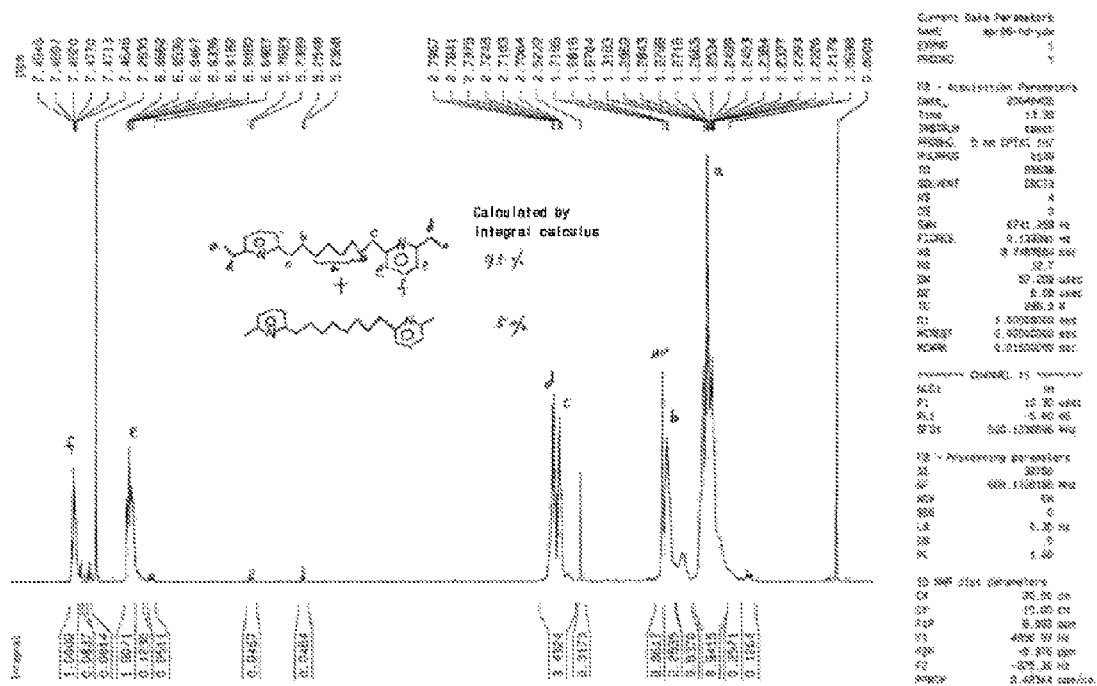
FIG. 2 is a $^1$H NMR spectrum of a compound prepared in Synthesis Example 1-(2)

The structure of the product was confirmed by $^1$H NMR analysis (FIG. 2). The spectral data for the product are as follows.

$^1$H NMR (CDCl$_3$): δ 1.1-1.4 (14H), 1.67 (4H), 2.72 (4H), 2.78 (4H), 6.94 (4H), 7.48 (2H)

1-(3) Preparation of initiator 2,7-dilithio{bis-1,8-[6-ethyl-2-pyridyl]}octane 2 g (5 mmol) of the product bis-1,8-{6-ethyl-2-pyridyl}octane was dissolved in 20 ml of anhydrous ethylbenzene and 1.4 g (12 mmol) of tetramethylethylenediamine in a 250 ml storage flask under a nitrogen atmosphere. To the solution was added dropwise 6.75 ml (11.3 mmol) of 1.5 M tert-butyl lithium with stirring to prepare the title initiator as a deep red solution.

1-(4) Identification of Active Sites

Figure 3:
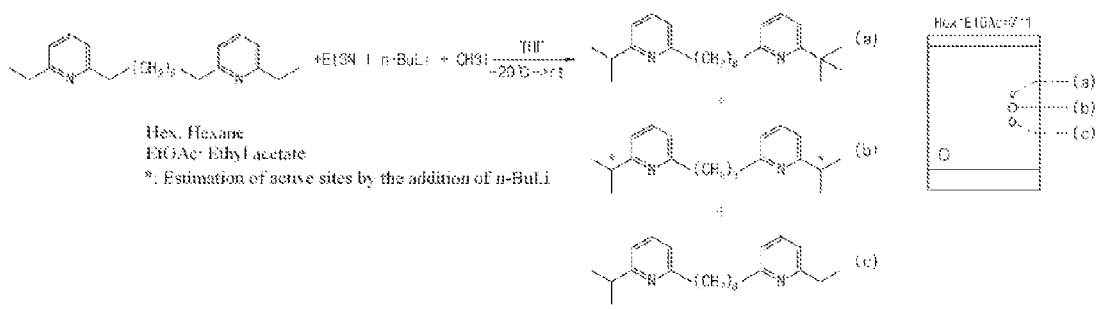
FIG. 3 shows experimental results for identifying the active sites of an initiator prepared in Synthesis Example 1-(3) by thin layer chromatography (TLC).

After (Et)$_3$N, n-BuLi and CH$_3$I were added to the initiator, thin layer chromatography (TLC) was performed (FIG. 3). The fact that the spots correspond to the compounds (a), (b) and (c) can be obviously predicted on the basis of organic chemistry knowledge.

From the TLC results, it can be confirmed that the active sites of the initiator are the same as shown in (b) (as the number of the methyl groups bonded to the molecule increases, the height of the spot on the TLC plate increases due to the increased non-polarity of the molecule. This fact can be generally understood by those with ordinary knowledge in the art of chemistry).

In the following examples, polymers were prepared using the organolithium initiator compound. Unless otherwise specified, all percentages (%) are by weight.

Example 1

100 g of styrene, 380 g of 1,3-butadiene and 3,000 g of n-hexane were added to a 10 L stainless steel reactor. The internal temperature of the reactor was adjusted to 50° C. with stirring. After the temperature reached 50° C., the initiator(2, 7-dilithio{bis-1,8-[6-ethyl-2-pyridyl]}octane) was added to the reactor. The initiator was used in an amount of 11 mmol, based on lithium. The adiabatic reaction was allowed to proceed with heating. Sixty minutes after the reaction initiation, 20 g of 1,3-butadiene was further added. After the reaction mixture was stirred at the same temperature for 30 min, 5 ml of glycidoxypropyltrimethoxysilane was added thereto. The resulting mixture was allowed to react with stirring for a given time. 5 g of butylated hydroxytoluene (BHT) as an antioxidant was added to the reactor to stop the reaction. The polymerization product was added to steam-heated water, stirred to remove the solvent, and roll-dried to remove the solvent residue and the water. The results of analysis of the polymerization product are shown in Table 1.

Example 2

The procedure of Example 1 was repeated, except that glycidoxypropyltrimethoxysilane was not added and 6 g (1 phi) of BHT as an antioxidant was added to stop the reaction. The polymerization product was treated by the same method as described in Example 1. The results of analysis of the polymerization product are shown in Table 1.

Comparative Example 1

The procedure of Example 1 was repeated, except that a 14.5% solution (7.2 ml, 11 mmol) of n-butyl lithium in hexane was used as an initiator. The polymerization product was treated by the same method as described in Example 1. The results of analysis of the polymerization product are shown in Table 1.

Comparative Example 2

The procedure of Example 1 was repeated, except that a solution of 1,3-diisopropenylbenzene/t-butyl lithium was used as a polymerization initiator. The initiator was prepared by the following procedure. 1,3-Diisopropenylbenzene (0.86 g) was dissolved in 20 ml of ethylbenzene and 5.2 g of tetramethylethylenediamine in a 250 ml storage flask under a nitrogen atmosphere. After the solution was cooled to −20° C. in a cooling bath, a 1.7 M solution (6 ml, 11 mmol) of tert-butyl lithium in pentene was added dropwise thereto with stirring. The cooling bath was removed and the reaction mixture was warmed to room temperature, affording the polymerization initiator as a reddish brown solution. The polymerization product was treated by the same method as described in Example 1. The results of analysis of the polymerization product are shown in Table 1.

Comparative Example 3

The procedure of Comparative Example 1 was repeated, except that glycidoxypropyltrimethoxysilane was not added and 6 g (1 phr) of BHT as an antioxidant was added to stop the reaction. The polymerization product was treated by the same method as described in Example 1. The results of analysis of the polymerization product are shown in Table 1.

TABLE 1

|  | Mooney viscosity ($ML_{1+4}$ at 100° C.) | Styrene content (%) | Vinyl content (%) |
| --- | --- | --- | --- |
| Example 1 | 51 | 20 | 63 |
| Example 2 | 53 | 19 | 62 |
| Comparative Example 1 | 49 | 19 | 55 |
| Comparative Example 2 | 47 | 21 | 53 |
| Comparative Example 3 | 46 | 20 | 54 |

Note:
* Mooney viscosity ($ML_{1+4}$ at 100° C.): Measured using a Mooney viscometer. Four minutes after each of the copolymers was preheated using a large-sized rotor at 100° C. for 1 min, a toque was measured.
* The styrene and vinyl contents in each of the polymers was measured based on the total amount of the polymer.

Example 3

In accordance with the composition shown in Table 2, the polymer prepared in Example 1 was blended with the other components.

Example 4

In accordance with the composition shown in Table 2, the polymer prepared in Example 2 was blended with the other components.

Comparative Example 4

In accordance with the composition shown in Table 2, the polymer prepared in Comparative Example 1 was blended with the other components.

Comparative Example 5

In accordance with the composition shown in Table 2, the polymer prepared in Comparative Example 2 was blended with the other components.

Comparative Example 6

In accordance with the composition shown in Table 2, the polymer prepared in Comparative Example 3 was blended with the other components.

TABLE 2

| Component | Content (phr) |
| --- | --- |
| Polymer | 100 |
| Stearic acid | 1.5 |
| ZnO | 2.5 |
| Silica (Zeosil 165N) | 80 |
| Aromatic oil | 40 |
| Bis-(triethoxysilylpropyl)tetrasulfane (Si-69) | 6.4 |
| Antioxidant (K-13) | 1.9 |
| Paraffin wax | 1.5 |
| t-Butylbenzothiazyl sulfonamide (TBBS) | 2.0 |
| 1,3-Diphenylguanidine (DPG) | 1.5 |
| Sulfur | 1.1 |

The compositions prepared in Examples 3-4 and Comparative Examples 4-6 were measured for hardness, tread wear and dynamic properties. For comparison, the results are shown in Table 3.

TABLE 3

| Measurement | | Example 3 | Example 4 | Comparative Example 4 | Comparative Example 5 | Comparative Example 6 |
|---|---|---|---|---|---|---|
| Initiator | — | EPO | EPO | n-BuLi | 1PB | n-BuLi |
| End substituent | — | Glymo | — | Glymo | Glymo | — |
| Tread wear (NBS) | Cc loss | 0.112 | 0.128 | 0.124 | 0.137 | 0.591 |
| Hardness (JIS) | Shore-A | 65 | 72 | 70 | 66 | 70 |
| Tan δ at 0° C. | DMTS | 0.7723 | 0.6771 | 0.6924 | 0.7729 | 0.6351 |
| Tan δ at 60° C. | DMTS | 0.1224 | 0.1590 | 0.1410 | 0.1026 | 0.1596 |

Note:
* EPO: Bis-1,8-(6-ethyl-2-pyridyl)octane/t-Butyl lithium
* 1PB: 1,3-Diisopropenylbenzene/t-Butyl lithium
* Glymo: Glycidoxypropyltrimethoxysilane The hardness of each of the compositions prepared in Examples 3-4 and Comparative Examples 4-6 was measured using a Shore A hardness tester, the tread wear of each of the vulcanized rubbers was measured using an NBS meter, and the Tan δ of each of the compositions, which represents the dynamic properties of the composition, was analyzed using a dynamic mechanical thermal spectrometer (DMTS, Gabo) at a frequency of 10 Hz and a strain of 7%.

A nuclear magnetic resonance (NMR) spectrometer was used to analyze the structure of the conjugated diene compound, the content ratio between the conjugated diene compound and the aromatic vinyl compound, and the random and block ratios of the conjugated diene compound to the aromatic vinyl compound.

The compositions of Examples 3 and 4, which comprise the polymers of Examples 1 and 2 whose ends were substituted with the alkoxysilane groups, respectively, showed better tread wear than the composition of Comparative Example 6. Further, although the terminal substituents of the polymers of Example 1 were the same as those of the polymers of Comparative Examples 1 and 2, the composition of Example 3 comprising the polymer of Example 1, which was prepared using the initiator of Formula 1, showed better tread wear than the composition of Comparative Example 4 comprising the polymer of Comparative Example 1 and the composition of Comparative Example 5 comprising the polymer of Comparative Example 2.

As explained in detail above, the living polymer of Formula 2 is prepared using the bifunctional polymerization initiator of Formula 1 containing amine moieties, and the ends of the living polymer are modified with an alkoxysilane compound to produce the rubber of Formula 3. When the rubber of Formula 3 is used as a tire material, it has a good affinity for silica as an inorganic reinforcing material. Further, the rubber of the present invention has a good affinity for carbon black as an organic reinforcing material due to the presence of amine moieties therein. Therefore, the rubber of the present invention exhibits greatly improved compatibility with silica and carbon black as reinforcing materials in the manufacture of a tire, compared to conventional rubber products. In conclusion, the rubber of the present invention can exhibit improved tread wear, high wet traction and low rolling resistance, which are physical properties required in tires, in all blends of fillers, e.g., when carbon black as an organic filler or silica as an inorganic filler is used alone or carbon black and silica are used as a mixture.

As is apparent from the foregoing, the copolymer of Formula 3 according to the present invention is prepared by copolymerization of a diene monomer with a vinyl aromatic monomer using the novel bifunctional initiator of Formula 1 in the presence of a hydrocarbon solvent to prepare the living polymer of Formula 2, and modifying both ends of the living polymer with an alkoxysilane compound. The copolymer of the present invention is useful in the manufacture of a tire. The copolymer of the present invention has an improved affinity for silica as an inorganic reinforcing material as well as carbon black as an organic reinforcing material in the manufacture of a tire. Therefore, the use of the copolymer according to the present invention can achieve desired physical properties of a tire, e.g., high wet traction, low rolling resistance and high tread wear.

What is claimed is:

1. An organolithium compound represented by Formula 1:

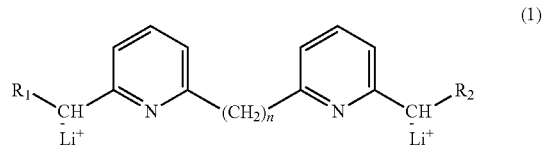

(1)

wherein $R_1$ and $R_2$, which are the same or different, each independently represent a $C_1$-$C_6$ alkyl group, and n is an integer in the range of 1 to 14.

2. The organolithium compound of claim 1, wherein the organolithium compound is used as a polymerization initiator.

3. An organolithium compound represented by Formula 2:

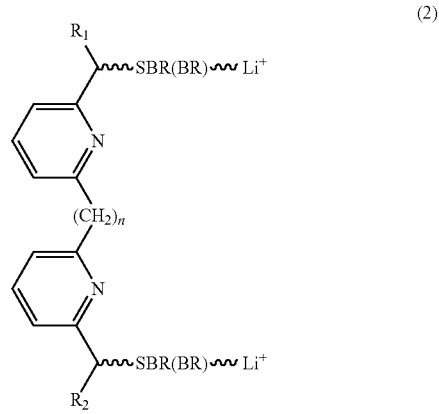

(2)

wherein $R_1$ and $R_2$, which are the same or different, each independently represent a $C_1$-$C_6$ alkyl group, and n is an integer in the range of 1 to 14.

4. A compound represented by Formula 3:

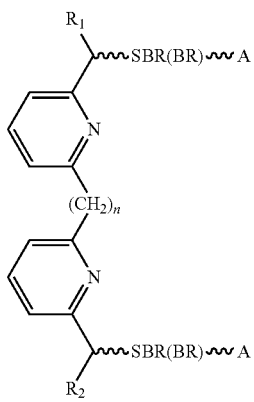

(3)

wherein $R_1$ and $R_2$, which are the same or different, each independently represent a $C_1$-$C_6$ alkyl group, n is an integer in the range of 1 to 14, and each A is an alkoxysilane group.

5. The compound of claim 4, wherein the compound is used as a tire material.

6. A composition comprising the compound of claim 4 and one or more reinforcing materials.

7. The composition of claim 6, further comprising one or more additives.

8. The composition of claim 6, wherein the composition is used as a tire material.

9. The composition of claim 7, wherein the composition is used as a tire material.

* * * * *